United States Patent
Morphy et al.

(10) Patent No.: US 7,126,027 B2
(45) Date of Patent: Oct. 24, 2006

(54) N-[(1-DIMETHYLAMINOCYCLOALKYL) METHYL]BENZAMIDE DERIVATIVES

(75) Inventors: John Richard Morphy, Newhouse (GB); Zoran Rankovoc, Newhouse (GB)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/484,410

(22) PCT Filed: Jul. 11, 2002

(86) PCT No.: PCT/EP02/07892

§ 371 (c)(1),
(2), (4) Date: Jul. 19, 2004

(87) PCT Pub. No.: WO03/010132

PCT Pub. Date: Feb. 6, 2003

(65) Prior Publication Data

US 2004/0242685 A1     Dec. 2, 2004

(30) Foreign Application Priority Data

Jul. 17, 2003   (EP) ................................ 01117273

(51) Int. Cl.
*C07C 233/65* (2006.01)
*A61K 31/165* (2006.01)

(52) U.S. Cl. ...................... 564/177; 514/617
(58) Field of Classification Search ................ 564/177; 514/617
See application file for complete search history.

(56) References Cited

U.S. PATENT DOCUMENTS

| 3,975,443 A | 8/1976 | Harper et al. |
| 4,049,663 A * | 9/1977 | Harper et al. ............... 546/233 |
| 4,346,101 A | 8/1982 | Lednicer |

OTHER PUBLICATIONS

Caulfield et al: "The first potent and selective Inhibitors of the Glycine Transporter Type 2"; J. Med. chem., vol. 44, No. 17, Aug. 16, 2001, pp. 2679-2682.
Werman, R. et al., "Evidence for Glycine As the Principal Transmitter Mediating Postsynaptic Inhibition in the Spinal Cord of the Cat," J. Gen. Phys., vol. 50 (1967) pp. 1093-1094.
Langosch, D. et al., "The inhibitory glycine receptor: A lignad-gated chloride channel of the central nervous system," Eur. J. Biochem., vol. 194 (1990) pp. 1-8.
Johnson, J. W. et al., "Glycine potentiates the NMDA response in cultured mouse brain neurons," Nature, vol. 325 (1987) pp. 529-531.
Ponce, J. et al., "Characterization of the 5' region of the rat brain glycine transporter GLYT2 gene: identification of a novel isoform," Neuroscience Letters, vol. 242 (1998) pp. 25-28.
Becker, C. M., "Convulsants Acting at the Inhibitory Glycine Receptor★," Handbook Exp. Pharmacol., vol. 102, Chapter 15 (1992) pp. 539-575.
Truong, D. D. et al., "Glycine Involvement in DDT-Induced Myoclonus," Movement Disorders, vol. 3, No. 1 (1988) pp. 77-87.
Simpson, Jr., R. K. et al., "Reduction in the Mechanonociceptive Response by Intrathecal Administration of Glycine and Related Compounds," Neurochemical Research, vol. 21, No. 10 (1996) pp. 1221-1226.
Yaksh, T. L., "Behavioral and autonomic correlates of the tactile evoked allodynia produced by spinal glycine inhibition: effects of modulatory receptor systems and excitatory amino acid antagonists," Pain, vol. 37 (1989) pp. 111-123.
Harper, N. J. et al., "1-(3,4-Dichlorobenzamidomethyl)cyclohexyldimethylamine and Related Compounds as Potential Analgesics," Journal of Medicinal Chemistry, vol. 17, No. 11 (1974), pp. 1188-1193.
Yang, D. et al., "Serotoninergic properties of new conformationally restricted benzamides,"Eur. J. Med. Chem., vol. 31 (1996) pp. 231-239.
Möhrle, H. et al., "Aminolyse Von 2-Phenylaziridin," Tetrahedron, vol. 27 (1971) pp. 1033-1041.

(Continued)

*Primary Examiner*—Shailendra Kumar
(74) *Attorney, Agent, or Firm*—Susan Hess; David H. Vickrey; Mark W. Milstead

(57) ABSTRACT

The present invention relates to N-[(1-dimethylaminocycloalkyl)methyl]benzamide derivatives having the general formula I Formula I

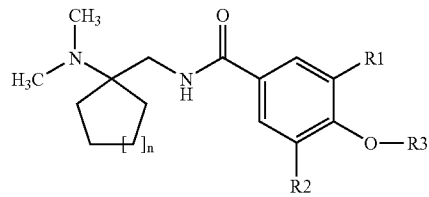

wherein n is 0, 1, 2 or 3; $R_1$ and $R_2$ are independently H, $(C_{1-4})$alkyl or $(C_{1-4})$alkyloxy;

$R_3$ is $(C_{3-8})$alkyl, $(C_{4-7})$cycloalkyl, $(C_{4-7})$cycloalkyl $(C_{1-3})$alkyl, $(C_{6-12})$aryl$(C_{1-3})$alkyl (wherein the aryl moiety is optionally substituted with 1–3 substituents selected from $(C_{1-4})$alkyl, $(C_{1-4})$alkyloxy, halogen, trifluoromethyl and methoxycarbonyl), or $(C_{4-9})$heteroaryl$(C_{1-3})$alkyl; or a pharmaceutically acceptable salt thereof. The invention also relates to pharmaceutical compositions comprising said derivatives, and to the use of these N-[(1-dimethylaminocycloalkyl)methyl]benzamide derivatives in the treatment of disorders or conditions which are responsive to inhibition of the GlyT-2 transporter, such as muscle spasticity, epilepsy and, particularly, acute, chronic and neuropathic pain.

9 Claims, No Drawings

OTHER PUBLICATIONS

Tilford, C. H. et al., "Substituted 3,4-Pentadienyldiamines as Inhibitors of Platelet Aggregation," Journal of Medicinal Chemistry, vol. 16, No. 6 (1973) pp.688-693.

Kasuga, K. et al., "Syntheses and Liquid Crystalline Properties of Homologous Series having Guaiacyl Structure as Central Linkage: 4-(4'-n-Alkoxy-3'-Methoxybenzoyl)-Oxybenzoic Acids," Cellulose Chem. Technol., vol. 19 (1985) pp. 37-45.

Kasztreiner, E. et al., "Derivatives of Alkoxybenzoic Acids, III," Acta Chimica Academiae Sci. Hung. Tomus, vol. 51, No. 3 (1967) pp. 327-337.

Klick, S. et al., "Glucosides and Glucose Esters of Hydroxybenzoic Acids in Plants," Phytochemistry, vol. 27, No. 7 (1988) pp. 2177-2180.

* cited by examiner

N-[(1-DIMETHYLAMINOCYCLOALKYL) METHYL]BENZAMIDE DERIVATIVES

This application is a 371 of PCT/EP02/07892, filed Jul. 11, 2002.

The invention relates to N-[(1-dimethylaminocycloalkyl)methyl]benzamide derivatives, to pharmaceutical compositions comprising the same as well as to the use of these N-[(1-dimethylaminocycloalkyl)methyl]benzamide derivatives in therapy.

N-[(1-Dimethylaminocyclohexyl)methyl]benzamide derivatives, wherein the benzamide phenyl moiety is substituted with up to three substituents such as halogen or methoxy groups, were disclosed in U.S. Pat. No. 3,975,443 (Harper & Hanburys Ltd.) as oral analgesics. Further N-[(1-dimethylaminocyclohexyl)methyl]benzamide compounds having additional substituents at the 4-position of the cyclohexyl group were disclosed in U.S. Pat. No. 4,346,101 as compounds with high analgesic potency and a low order of sedative activity. Since these early developments our knowledge of mechanistic aspects of neurotransmission has much broadened. Glycine is one of the major inhibitory neurotransmitters in the spinal cord and brainstem of vertebrates (Aprison et al., *J. Gen. Phys.* 1967, 50, 1093–1094). The inhibitory actions of glycine are mediated by the strychnine-sensitive glycine receptor (ssGlyR), a ligand gated chloride channel distributed throughout the spinal cord and the brain stem (Becker et al., *Eur. J. Biochem.*, 1990, 194, 1–8). Glycine is also known to potentiate the action of glutamate acting as an essential co-agonist on postsynaptic N-methyl-D-aspartate (NMDA) receptors (Johnson and Ascher, *Nature*, 1987, 325, 529–531). Synaptic levels of glycine are believed to be controlled by high affinity glycine transporters. These transporters are members of a large family of sodium/chloride-dependant transporters, which are composed of single oligomeric proteins containing 12 hydrophobic membrane-spanning domains. Molecular cloning has revealed the existence of two major classes of glycine transporter subtypes, termed type 1 (GlyT-1) and type 2 (GlyT-2) (Aragon, et al., *Neurosci. Lett.* 1998 242, 25–28). These have been further divided into three subtypes of GlyT-1 (a, b and c) and two splice variant versions of GlyT-2 (a and b). Recent immunocytochemical studies showed that the GlyT-1 transporter has a wide distribution throughout the CNS whereas the GlyT-2 transporter has a similar distribution to ssGlyR, being confined to the spinal cord and the brain stem only.

By regulating the synaptic level of glycine, the GlyT-1 and GlyT-2 transporters are expected to selectively influence the activity at the NMDA and ssGlyR receptors, respectively. There is evidence that glycine-mediated inhibition produces muscle relaxation and blockade of this inhibition produces convulsions (Becker C. M. *Handb. Exp. Pharmacol.*, 1992, 102, 539–575). Thus, an increase of endogenous levels of glycine by inhibition of the GlyT-2 transporter might provide skeletal muscle relaxation, which is useful in treatment of diseases or conditions associated with increased muscle contraction, such as muscle spasticity (Truong et al., *Movement Disorders*, 1988, 3, 77–89) and epilepsy. Glycine also has an important role in the modulation of nociceptive pathways (Goodman et al., *Neurochem. Res.* 1996, 21, 1221–1226). Inhibitors of the GlyT-2 transporter can be used to increase endogenous levels of glycine and therefore enhance activity of inhibitory neurons expressing ssGlyR thus diminishing the transmission of pain-related (i.e. nociceptive) signal, shown to be mediated by this receptor (Yaksh, *Pain*, 1989, 37, 111–123). Therefore, an increase in synaptic levels of endogenous-glycine by a selective inhibition of the GlyT-2 transporter in the spinal cord offers possibilities for the development of analgesic agents, in particularly for treatment of neuropathic pain, which are devoid of CNS side effects that are characteristic for current μ-opioid analgesics.

Neuropathic pain syndromes are difficult to treat Several classes of drugs have limited efficacy, but complete pain control is rarely achieved. Thus, there remains a need for compounds with a high analgesic potency and with minimal CNS related side effects.

It has now been found that N-[(1-dimethylaminocycloalkyl)methyl]benzamide derivatives having the general formula I

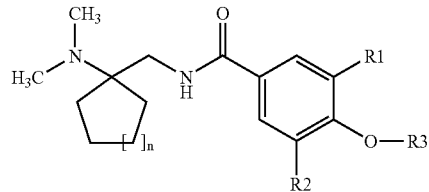

Formula I wherein n is 0, 1, 2 or 3;

$R_1$ and $R_2$ are independently H, $(C_{1-4})$alkyl or $(C_{1-4})$alkyloxy;

$R_3$ is $(C_{3-8})$alkyl, $(C_{4-7})$cycloalkyl, $(C_{4-7})$cycloalkyl$(C_{1-3})$alkyl, $(C_{6-12})$aryl$(C_{1-3})$alkyl (wherein the aryl moiety is optionally substituted with 1–3 substituents selected from $(C_{1-4})$alkyl, $(C_{1-4})$alkyloxy, halogen, trifluoromethyl and methoxycarbonyl), or $(C_{4-9})$heteroaryl$(C_{1-3})$-alkyl; or a pharmaceutically acceptable salt thereof; are glycine re-uptake inhibitors selective for the GlyT-2 transporter, which can therefore be used in the treatment of diseases and conditions associated with the glycinergic system, e.g. muscle spasticity, epilepsy and, particularly, acute, chronic and neuropathic pain.

The term $(C_{1-4})$alkyl, as used in the definition of formula I, means a branched or unbranched alkyl group having 1–4 carbon atoms, like butyl, isobutyl, tertiary butyl, propyl, isopropyl, ethyl and methyl. A preferred $(C_{1-4})$alkyl group is methyl.

In the term $(C_{1-4})$alkyloxy, $(C_{1-4})$alkyl has the meaning as defined above. A preferred $(C_{1-4})$alkyloxy group is methyloxy.

The term $(C_{3-8})$alkyl means a branched or unbranched alkyl group having 3–8 carbon atoms, such as propyl, butyl, isobutyl, pentyl, isopentyl, neopentyl, hexyl, heptyl and octyl. Preferred are n-butyl, isobutyl and pentyl.

The term $(C_{4-7})$cycloalkyl means a cyclic alkyl group having 4–7 carbon atoms, like cyclobutyl, cyclopentyl, cyclohexyl and cycloheptyl.

The term $(C_{4-7})$cycloalkyl$(C_{1-3})$alkyl means a $(C_{1-3})$alkyl group which is substituted with a $(C_{4-7})$cycloalkyl group, both groups having the meaning as defined above. Examples are cyclohexylmethyl, cyclopentylmethyl, 1-(cyclohexyl)ethyl, and the like.

The term $(C_{6-12})$aryl$(C_{1-3})$alkyl means a $(C_{1-3})$alkyl group which is substituted with a $(C_{6-12})$aryl group. The term $(C_{6-12})$aryl means an aromatic group having 6–12 carbon atoms like for example phenyl, naphthyl or biphenyl. An example of a $(C_{6-12})$aryl$(C_{1-3})$-alkyl is the benzyl group.

The term $(C_{4-9})$heteroaryl$(C_{1-3})$alkyl means a $(C_{1-3})$alkyl group which is substituted with a $(C_{4-9})$heteroaryl group. The term $(C_{4-9})$heteroaryl means a heteroaromatic group having 4–9 carbon atoms and one or more heteroatoms selected from O, S and N, such as for example thienyl, furanyl, pyridyl, indolyl, benzoxazolyl, benzthiazolyl and the like. Preferred ($C_{4-9}$)heteroaryl($C_{1-3}$)alkyl groups are (thien-3-yl)methyl and (furan-3-yl)methyl.

The term halogen means F, Cl, Br, or I. When halogen is a substituent at an alkyl group, F is preferred. A preferred halogen substituted alkyl group is trifluoromethyl.

Preferred are the N-[(1-dimethylaminocycloalkyl)methyl] benzamide derivatives of formula I wherein n is 0 or 1, i.e. the N-[(1-dimethylaminocyclopentyl)methyl]benzamide- and the N-[(1-dimethylaminocyclobutyl)methyl]benzamide derivatives.

More preferred are the compounds of formula I wherein R1 and R2 are independently methyl or methyloxy.

Especially preferred compounds of the invention are:
4-benzyloxy-3,5-dimethoxy-N-[(1-dimethylaminocyclopentyl)methyl]benzamide;
4-benzyloxy-3,5-dimethyl-N-[(1-dimethylaminocyclobutyl)methyl]benzamide;
4-benzyloxy-3,5-dimethyl-N-[(1-dimethylaminocyclopentyl)methyl]benzamide;
3,5-dimethoxy-4-(4-methylbenzyloxy)-N-[(1-dimethylaminocyclopentyl)methyl]benzamide;
3,5-dimethoxy-4-(1-phenyl)ethoxy-N-[(1-dimethylaminocyclopentyl)methyl]benzamide and
4-(4-chlorobenzyloxy)-3,5-dimethoxy-N-[(1-dimethylaminocyclopentyl)methyl]benzamide.

The N-[(1-dimethylaminocyclohexyl)methyl]benzamide derivatives of the invention differ structurally from the known analgesic compounds from U.S. Pat. No. 3,975,443 (Harper & Hanburys Ltd.) in having a bulky O-substituent at the 3-position of the benzamide group.

The compounds of the invention can be prepared by methods known in the art of organic chemistry in general. More specifically such compounds can be prepared using procedures outlined by Harper et al. (J. Med. Chem. 1974, 17, 1188–1193) or using modifications of those routes.

N-[(1-dimethylaminocycloalkyl)methyl]benzamide derivatives of formula I can for example be prepared from the acylation of a 1-dimethylamino-1-aminomethylcycloalkane of formula II, wherein n is 0, 1, 2 or 3, by a substituted benzoic acid derivative of formula III, wherein R1, R2 and R3 have the meanings as previously defined, upon in situ activation of the carboxylic acid group with activating agent such as dicyclohexylcarbodiimide, benzotriazole-1-yl-oxy-tris-pyrrolidinophosphonium hexafluorophosphate (PyBOP®), 2-(1H-benzotriazole-1-yl)-1,1,3,3-tetramethyluronium tetrafluoroborate (TBTU) and the like, or alternatively, by initial conversion of the carboxylic acid derivative III to the corresponding carboxylic acid chloride followed by acylation of compounds of formula II.

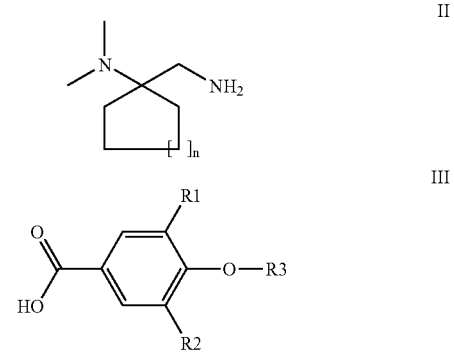

Compounds of formula II can prepared by reduction, using for example $AlH_3$, of the appropriate aminonitrile of formula IV, which itself can be prepared by a Strecker synthesis involving the appropriate ketone of formula V and dimethylamine.

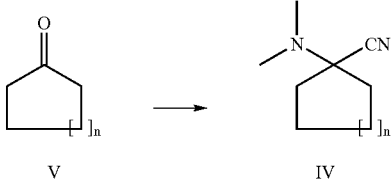

Benzoic acid derivatives of formula III are either commercially available or can be prepared using methods known in the art.

Pharmaceutically acceptable salts may be obtained by treating the free base of a compound according to formula I with a mineral acid such as hydrochloric acid, hydrobromic acid, phosphoric acid and sulphuric acid, or an organic acid such as for example ascorbic acid, citric acid, tartaric acid, lactic acid maleic acid, malonic acid, fumaric acid, glycolic acid, succinic acid, propionic acid, acetic acid, methane sulphonic acid, and the like.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a N-[(1-dimethylaminocycloalkyl) methyl]benzamide derivative having the general formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, intramuscular, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

EXAMPLE 1

4-Butyloxy-3,5-dimethoxy-N-[(1-dimethylaminocyclohexyl)methyl]benzamide

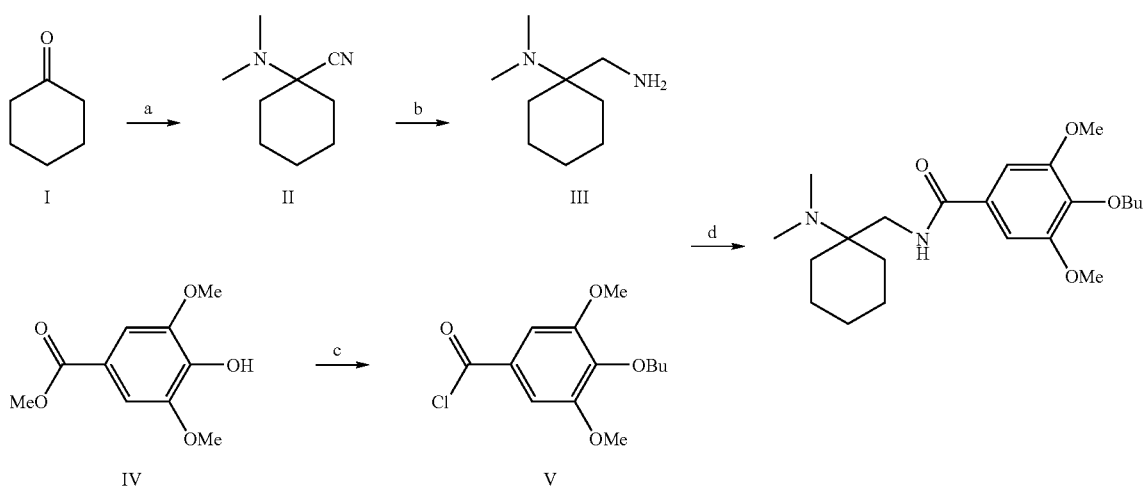

(a) Me$_2$H$_2$N$^+$Cl$^-$, KCN (aq), 18 h;
(b) H$_2$SO$_4$, LiAlH$_4$, THF, 0° C. to 20° C., 18 h;
(c) BuBr, K$_2$CO$_3$, acetophenone, 135° C., 18 h; KOH, MeOH, 65° C.; SOCl$_2$, toluene, 110° C.;
(d) Et$_3$N, THF.

The invention further includes a pharmaceutical composition, as hereinbefore described, in combination with packaging material suitable for said composition, said packaging material including instructions for the use of the composition for the use as hereinbefore described.

The N-[(1-dimethylaminocycloalkyl)methyl]benzamide derivatives of the invention are selective inhibitors of the GlyT-2 transporter, as compared to the GlyT-1 transporter, as can be measured with the use CHO cells stably transfected with either human transporter GlyT-2 or human transporter GlyT-1.

Compounds of the invention, as exemplified by 4-benzyloxy-3,5-dimethoxy-N-[(1-dimethylaminocyclopentyl)methyl]benzamide, reduce the mechanical allodynia observed in the Chung in vivo model of neuropathy.

The compounds may therefore be used in the treatment of a disorder or condition which is responsive to inhibition of the GlyT-2 transporter, such as muscle spasticity, epilepsy, and, particularly, acute, chronic and neuropathic pain.

The compounds of the invention may be administered for humans in a dosage of 0.001–50 mg per kg body weight, preferably in a dosage of 0.1–20 mg per kg body weight.

The invention is illustrated by the following Examples.

General Chemical Procedures

All reagents were either purchased from common commercial sources or synthesised according to literature references using commercial sources. Proton NMR ($^1$H NMR) were obtained on a Bruker DPX 400 spectrometer and are referenced to internal TMS. Mass spectra were recorded on a Shimadzu LC-8A (HPLC) PE Sciex API 150EX LCMS. Analytical reversed-phase LCMS analysis was carried out on LUNA C18 column (5μ; 30×4.6 mm) under gradient conditions (90% water/0.1% formic acid to 90% acetonitrile/0.1% formic acid) at a flow rate of 4 mL/min.

(a): 1-Dimethylamino-cyclohexane-1-carbonitrile (II).[1]

A solution of potassium cyanide (8.3 g, 0.1 mol) in water (50 mL) was added to a suspension of dimethylamine hydrochloride (8.3 g, 0.1 mol) in cyclohexanone (10 g, 0.1 mol) over 10 min at 0° C. The mixture was stirred for 18 h at room temperature, then the product was extracted into ether (40 mL) and washed with water (3×20 mL), dried over MgSO$_4$ and evaporated under reduced pressure to give the title compound II as a colourless oil (13.3 g, 98%). $^1$H NMR (CDCl$_3$) δ 1.23, (m, 1H), 1.48 (m, 4H), 1.69 (m, 1H), 1.75 (m, 2H), 2.09 (m, 2H), 2.34 (s, 6H). MS m/z 153 (MH$^+$).

(b): (1-Dimethylaminocyclohexyl)methylamine (III).[1]

A solution of conc. sulphuric acid (7.0 mL, 0.131 mol) and anhydrous tetrahydrofuran (THF; 25 mL), cooled to 0° C., was added dropwise into a stirred suspension of lithium aluminium hydride (10.0 g, 0.263 mol) in anhydrous THF (160 mL) at 0° C. under nitrogen atmosphere. The mixture was allowed to warm to room temperature over 1 h and then left to rest overnight at room temperature. A solution of 1-dimethylaminocyclohexane-1-carbonitrile (II; 13.3 g, 0.88 mol) and anhydrous THF (60 mL) was added dropwise into the vigorous stirred reaction suspension at 0° C. under nitrogen atmosphere. The reaction mixture was stirred at 40° C. for 1 h. The reaction was then cooled to 0° C. and quenched with water (20 mL). Inorganic residues were removed by filtration and the filtrate concentrated under reduced pressure. Vacuum distillation of the crude material produced 4.3 g (32%) of pure amine as a colourless oil. $^1$H NMR (CDCl$_3$) δ: 1.35, (m, 2H), 1.46 (s, 2H), 1.58 (m, 4H), 1.73 (m, 2H), 2.23 (s, 6H), 2.65 (s, 2H). MS m/z 143.2 (MH$^+$).

(c): 4-Butyloxy-3,5-dimethoxybenzoyl chloride (V).

Methyl syringate (10 g, 0.047 mol) and potassium carbonate (8.5 g, 0.061 mol) were stirred in acetophenone (100 mL) at 135° C. Butyl bromide (6.6 mL, 0.061 mol) was added dropwise over 1.5 h and the reaction was stirred over 18 h at 135° C. The reaction was cooled, filtered and the inorganic solids washed with acetone (20 mL). The combined filtrate was concentrated under high vacuum to give a red oil which was redissolved in ether (50 mL) and washed with 2N aqueous NaOH (2×10 mL) and water (3×10 mL). The organic layer was dried using anhydrous $NaSO_4$ and the solvent removed under reduced pressure. The crude product was redissolved in methanol (250 mL) followed by addition of aqueous potassium hydroxide (44%, 20 mL). After heating at reflux for 2 h the reaction mixture was allowed to cool down to room temperature and left to rest over 18 h. The solvent was then concentrated under reduced pressure, the residue reconstituted in water (100 mL) and the resulting aqueous solution washed with ether (3×30 mL). The aqueous layer was acidified to pH=1 with 5N HCl and the precipitated product collected by filtration. The crude product was recrystallised from methanol to give 6.1 g, 51% yield of 4-butyloxy-3,5-dimethoxybenzoic acid as a colourless solid. $^1$H NMR ($CDCl_3$) δ: 0.98 (t, J=5.1 Hz, 3H), 1.49 (m, 2H), 1.74 (m, 2H), 3.91 (s, 6H), 4.06 (t, J=5 Hz, 2H), 7.37 (s, 2H). MS m/z 255.4 ($MH^+$).

A mixture of 4-butyloxy-3,5-dimethoxybenzoic acid (5.0 g, 0.0197 mol) and thionyl chloride (10 mL) in toluene (10 mL) was heated at 90° C. for 18 h. The reaction mixture was concentrated under reduced pressure. To remove excess of thionyl chloride the residue was repeatedly redissolved in toluene (3×20 mL) and the resulting solution evaporated to dryness to obtain 4-butyloxy-3,5-dimethoxybenzoyl chloride (5.3 g, 99% yield) as a pale yellow oil. $^1$H NMR ($CDCl_3$) δ: 0.99 (t, J=5.0 Hz, 3H), 1.47 (m, 2H), 1.73 (m, 2H), 3.90 (s, 6H), 4.09 (t, J=5.1 Hz, 2H), 7.36 (s, 2H).

(d): 4-Butyloxy-3,5-dimethoxy-N-[1-(dimethylaminocyclohexyl)methyl]benzamide.

A solution of acid chloride V (4.4 g, 0.016 mol) in anhydrous THF (10 mL) was added dropwise over 15 min into a solution of amine III (2.5 g, 0.016 mol) and triethylamine (2.5 mL, 0.017 mol) in THF (20 mL) at 0° C. The reaction was allowed to warm to room temperature and stirred for 48 h. The solvent was removed under reduced pressure and the residue partitioned between 5% aqueous $Na_2CO_3$ solution (40 mL) and ethyl acetate (40 mL). The organic layer was washed with fresh 5% aqueous $Na_2CO_3$ solution (20 mL), brine (20 mL), dried over $Na_2SO_4$ and evaporated to dryness. The residue was redissolved in methanolic hydrogen chloride (20 mL) and the solvent removed under reduced pressure. The crude product was recrystallised from hot ethanol to obtain 4-butyloxy-3,5-dimethoxy-N-[(1-dimethylaminocyclohexyl)methyl]benzamide (4.96 g, 79% yield) as a colourless solid.

$^1$H NMR (MeOD) δ: 0.98 (t, J 5.2 Hz, 3H), 1.49 (m, 8H), 1.67 (m, 4H), 1.72 (m, 2H) 2.3 (s, 6H), 3.52 (d, J=4.3 Hz, 2H), 3.89 (s, 6H), 3.99 (t, J=5.3 Hz, 2H), 6.91 (bs, 1H), 7.0 (s, 2H). MS m/z 393.4 ($MH^+$). Anal. ($C_{22}ClH_{37}N_2O_4.0.125H_2O$) C, H, N, Cl.

EXAMPLE 2

4-Benzyloxy-3,5-dimethoxy-N-[1-(dimethylaminocyclopentyl)methyl]benzamide

Prepared from 1-(dimethylaminocyclopentyl)methylamine (1.7 g, 0.02 mol) and 4-benzyloxy-3,5-dimethoxybenzoyl chloride[6] (3.71 g, 0.012 mol) by the method used in Example 1. The hydrochloride salt was recrystallised from methanol/ether mixture (4/1) to obtain the product (1.95 g; 32%) as a colourless solid. $^1$H NMR (MeOD) δ: 1.88 (m, 6H), 2.05 (m, 2H), 2.97 (s, 6H), 3.76 (s, 2H), 3.88 (s, 6H), 5.03 (s, 2H), 7.24 (s, 2H), 7.30 (m, 3H), 7.44 (m, 2H). LCMS m/z 413.3 ($MH^+$; 98.7%). HRMS (FAB) calc. 413.2434, found 413.2447. Anal. ($C_{24}ClH_{33}N_2O_4.0.125H_2O$) C, H, N, Cl.

EXAMPLE 3

4-n-Butyloxy-3-methoxy-N-[1-[(dimethylaminocyclohexyl)methyl]benzamide

Synthesised from 1-(dimethylaminocyclohexyl)methylamine (Example 1(b) and 4-butyloxy-3-methoxybenzoyl chloride as described in Example 1 (d) and purified by LCMS to obtain the product as a trifluoroacetate salt. $^1$H NMR ($CDCl_3$) δ: 0.97 (t, 3H, J=4 Hz), 1.17 (m, 1H), 1.48 (m, 2H), 1.65 (m, 3H), 1.82 (m, 6H), 2.01 (d, 2H, J=3 Hz), 2.79 (s, 6H), 3.98 (s, 3H), 4.05 (m, 4H), 6.92 (d, 1H, J=4 Hz), 7.78 (s, 1H), 7.85 (d, 1H, J=4 Hz), 8.57 (m, 1H), 11.80 (s, 1H). LCMS m/z 363.2 ($MH^+$; 95.5%). HRMS (FAB) calc. 363.2639, found 363.2653.

EXAMPLE 4

4-n-Butyloxy-3,5-dimethoxy-N-[(1-(ethylmethylamino)cyclohexyl)methyl]benzamide

Synthesised from [1-(ethylmethylamino)cyclohexyl]methylamine and 4-butyloxy-3,5-dimethoxybenzoyl chloride V, following procedure described in Example 1 and purified by LCMS to obtain the product as a trifluoroacetate salt. $^1$H NMR ($CDCl_3$) δ: 0.94 (t, 3H, J=4 Hz), 1.15 (m, 1H), 1.48 (m, 3H), 1.58 (t, 3H, J=4 Hz), 1.65 (m, 3H), 1.73 (m, 3H), 1.81 (m, 3H), 2.09 (d, 2H, J=4 Hz), 2.77 (d, 2H, J=2 Hz), 2.82 (m, 1H), 3.54 (m, 1H), 3.96 (s, 6H), 4.01 (t, 2H, J=4 Hz), 4.06 (m, 1H), 4.20 (dd, 1H, J=3 Hz), 7.57 (s, 2H), 9.05 (m, 1H), 11.62 (s, 1H). LCMS m/z 407.4 ($MH^+$; 98.8%). HRMS (FAB) calc. 407.2898, found 407.2910.

EXAMPLE 5

4-Benzyloxy-3,5-dimethoxy-N-[(1-dimethylaminocyclohexyl)methyl]benzamide

Prepared, following procedure described in Example 1, from 1-(dimethylaminocyclohexyl)methylamine III and 4-benzyloxy-3,5-dimethoxybenzoyl chloride[6] and purified by LCMS to obtain the product as a trifluoroacetate salt. $^1$H NMR ($CDCl_3$) δ: 1.65 (m, 2H), 1.76 (m, 3H), 1.85 (m, 3H), 1.97 (d, 2H, J=4 Hz), 2.83 (m, 6H), 3.88 (s, 6H), 4.06 (d, 2H, J=3 Hz), 5.05 (s, 2H), 7.21 (s, 2H), 7.32 (m, 3H), 7.48 (d, 2H, J=3 Hz), 8.55 (m, 1H), 11.66 (s, 1H). LCMS m/z 427.2 ($MH^+$; 94.5%). HRMS (FAB) calc. 427.2588, found 427.2605.

EXAMPLE 6

4-n-Butyloxy-N-[(1-dimethylaminocyclohexyl)methyl]benzamide

Synthesised from 1-(dimethylaminocyclohexyl)methylamine and 4-butyloxy benzoyl chloride following the procedure of Example 1 (g and purified by LCMS to obtain the product as a trifluoroacetate salt. $^1$H NMR ($CDCl_3$) δ: 0.97 (t, 3H, J=4 Hz), 1.18 (m, 1H), 1.49 (m, 2H), 1.67 (m, 4H), 1.80 (m, 5H), 2.01 (d, 2H, J=3 Hz), 2.79 (s, 6H), 4.01 (m, 4H), 6.93 (d, 2H, J=4 Hz), 8.18 (d, 2H, J=4 Hz), 8.47 (m, 1H), 11.90 (s, 1H). LCMS m/z 333.2 (MH$^+$; 96.5%). HRMS (FAB) calc. 333.2539, found 333.2536.

EXAMPLE 7

4-n-Butyloxy-3,5-dimethoxy-N-[(1-dimethylaminocyclopentyl)methyl]benzamide

Synthesised, following the procedure as described in Experiment 2, from 1-(dimethylaminocyclopentyl) methylamine[1] and 4-butyloxy-3,5-dimethoxybenzoyl chloride V and purified by LCMS to obtain the product as a triflouroacetate salt. $^1$H NMR (CDCl$_3$) δ: 0.94 (t, 3H, J=4 Hz), 1.48 (m, 2H), 1.74 (m, 2H), 1.82 (m, 2H), 1.90 (m, 2H), 1.95 (m, 2H), 1.99 (m, 2H), 2.80 (s, 6H), 3.86 (s, 2H), 3.96 (s, 6H), 4.02 (t, 2H, J=3 Hz), 7.51 (s, 2H), 8.74 (m, 1H), 12.37 (s, 1H). LCMS m/z 379.4 (MH$^+$; 98.5%). HRMS (FAB) calc. 379.2594, found 379.2592.

EXAMPLE 8

4-Benzyloxy-3,5-dimethyl-N-[1-(dimethylaminocyclobutyl)methyl]benzamide (a): 1-Dimethylamino-1-cyclobutylcarbonitrile was prepared from cyclobutanone (2.1 mL, 0.0285 mol) by the method used in Example 1 (Step a) as a clear oil in 96% yield.

$^1$H NMR (CDCl$_3$) δ: 1.91 (m, 1H), 2.08 (m, 1H), 2.18 (s, 6H), 2.22 (m, 2H), 2.39 (m, 2H). MS 125.1 (MH$^+$). (1-Dimethylaminocyclobutyl)methylamine was prepared from 1-dimethylamino-1-cyclobutylcarbonitrile (0.028 mol) by the method used in Example 1 (Step B) as a clear oil in 41% yield (1.49 g). $^1$H NMR (CDCl$_3$) δ 1.66 (m, 4H), 2.06 (m, 2H), 2.24 (s, 6H), 2.45 (s, 2H), 2.85 (s, 2H). MS m/z 129.1 (MH$^+$).

(b): The title compound was prepared from (1-dimethylaminocyclobutyl)methylamine (0.05 g, 0.39 mmol) and 4-butyloxy-3,5-dimethylbenzoyl chloride (0.107 g, 0.39 mmol) by the method used in Example 1 (Step d). The product was purified by HPLC and isolated as the trifluoroacetate salt, 0.047 g of clear oil, 30% yield. $^1$H NMR (CDCl$_3$) δ: 1.98 (m, 2H), 2.14 (m, 2H), 2.30 (s, 6H), 2.48 (m, 2H), 2.81 (s, 6H), 3.98 (d, 2H, J~3 Hz), δ 4.82 (s, 2H), 7.38 (m, 3H), 7.45 (m, 2H), 7.57 (s, 2H), 8.0 (m, 1H), 11.7 (s, 1H). LCMS m/z 367.0 (MH+; 100%).

EXAMPLE 9

4-Benzyloxy-3,5-dimethyl-N-[(1-dimethylaminocyclopentyl)methyl]benzamide

Prepared from (1-dimethylaminocyclopentyl)methylamine (1.0 g, 0.007 mol) and 4-butyloxy-3,5-dimethylbenzoyl chloride (1.9 g, 0.007 mol) by the method used in Example 1 (Step d). The product was converted to the hydrochloride salt and recrystallised from ethanol with addition of diethyl ether, 1.6 g of colourless solid, 55% yield.

$^1$H NMR (MeOD) δ: 1.88 (m, 4H), 1.98 (m, 2H), 2.08 (m, 2H), 2.31 (s, 6H), 2.97 (s, 6H), 3.74 (s, 2H), 4.88 (s, 2H), 7.38 (m, 3H), 7.45 (m, 2H), 7.60 (s, 2H). MS 381.2 (MH+). HPLC 98.7%. LCMS m/z 381.4 (MH+; 100%).

EXAMPLE 10

3,5-Dimethoxy-4-(4-methylbenzyloxy)-N-[(1-dimethylaminocyclopentyl)methyl]benzamide (a):. A suspension of 4-benzyloxy-3,5-dimethyl-N-[(1-dimethylaminocyclobutyl)methyl]-benzamide (10 mmol) and palladium on charcoal (5%, 1 mmol) in ethanol (100 mL) was stirred under hydrogen atmosphere (1 atm) at room temperature over 18 h. The suspension was filtered over celite and the filtrate concentrated under vacuum to obtain the crude 3,5-dimethoxy-4-hydroxy-N-[(1-dimethylaminocyclopentyl)methyl]benzamide.

$^1$H NMR (CDCl$_3$) δ: 1.94 (m, 2H), 2.12 (m, 2H), 2.31 (s, 6H), 2.44 (m, 2H), 2.77 (s, 6H), 3.95 (d, 2H, J~3 Hz) and 7.3 (s, 2H). MS m/z 276.0 (MH+).

(b): A suspension of 4-methylbenzyl bromide (1 mmol), the product obtained under (a) (1 mmol) and caesium carbonate (5 mmol) in dimethylformamide (40 mL) was heated at 80° C. under vigorous stirring over 18 h. The reaction mixture was filtered to remove caesium carbonate and the filtrate concentrated. The title compound product was purified by HPLC and isolated as the trifluoroacetate salt. $^1$H NMR (CDCl$_3$) δ: 1.85 (m, 4H), 1.98 (m, 4H), 2.33 (s, 3H), 2.86 (d, 6H, J~2 Hz), 3.84 (s, 6H), 3.85 (m, 2H), 5.02 (s, 2H), 7.10 (s, 2H), 7.15 (d, 2H, J~3 Hz), 7.35 (d, 2H, J~3 Hz), 8.34 (m, 1H), 10.95 (s, 1H). LCMS m/z 427.2 (MH+; 100%).

EXAMPLE 11

3,5-Dimethoxy-4-(1-phenyl)ethoxy-N-[1-(dimethylaminocyclopentyl)methyl]benzamide Synthesised from 1-(phenyl)ethyl bromide and 3,5-dimethoxy-4-hydroxy-N-[(1-dimethylaminocyclopentyl)methyl]benzamide following the procedure as described in Example 10 (b). The crude product was purified by HPLC and isolated as the trifluoroacetate salt.

$^1$H NMR (CDCl$_3$) δ: 1.60 (d, 3H, J~3 Hz), 1.85 (m, 4H), 1.95 (m, 4H), 2.84 (d, 6H, J~2 Hz), 3.84 (m, 8H), 5.43 (q, 1H, J~3 Hz), 7.07 (s, 2H), 7.25 (m, 3H), 7.44 (d, 2H, J~3 Hz), 8.34 (m, 1H), 11.28 (s, 1H). LCMS m/z 427.2 (MH+; 100%).

EXAMPLE 12

4-(4-Chloro)benzyloxy-3,5-dimethoxy-N-[1-(dimethylaminocyclopentyl)methyl]benzamide Synthesised from 4-chlorobenzyl bromide and 3,5-dimethoxy-4-hydroxy-N-[(1-dimethylaminocyclopentyl)methyl]benzamide following the procedure as described in Example 10 (b). The crude product was purified by SPE chromatography. $^1$H NMR (CDCl$_3$) δ: 1.45 (m, 2H), 1.65 (m, 4H), 1.83 (m, 2H), 2.29 (s, 6H), 3.45 (d, 2H, J~2 Hz), 3.8 (s, 6H), 5.02 (s, 2H), 6.98 (m, 1H), 7.0 (s, 2H), 7.3 (d, 2H, J~3 Hz), 7.41 (d, 2H, J~3 Hz). LCMS m/z 447.0 (MH+; 99%).

EXAMPLE 13

4-(Cyclohexylmethoxy)-3,5-dimethoxy-N-[(1-dimethylaminocyclohexyl)methyl]benzamide Synthesised from cyclohexylmethyl bromide and 3,5-dimethoxy-4-hydroxy-N-[(1-dimethylaminocyclohexyl)methyl]benzamide following the procedure as described in Example 10 (b). The crude product was purified by HPLC and isolated as the trifluoroacetate salt. $^1$H NMR (CDCl$_3$) δ: 1.05 (m, 2H), 1.25 (m, 6H), 1.58 (m, 5H), 1.85 (m, 8H), 2.83 (d, 6H, J~2 Hz), 3.90 (d, 2H, J~3 Hz), 3.88 (s, 6H), 4.05 (d, 2H, J~3 Hz), 7.21 (s, 2H), 8.50 (m, 1H), 11.65 (s, 1H). LCMS m/z 433.4 (MH+; 100%).

EXAMPLE 14

3,5-Dimethoxy-4-(4-trifluoromethylbenzyloxy)-N-[(1-dimethylaminocyclopentyl)methyl]benzamide Synthesised from 4-trifluoromethylbenzyl bromide and 3,5-dimethoxy-4-hydroxy-N-[(1-dimethylaminocyclopentyl)methyl]benzamide following the procedure as described in Example 10 (b). The crude product was purified by HPLC and isolated as the trifluoroacetate salt. $^1$H NMR (CDCl$_3$) δ: 1.85 (m, 4H), 1.98 (m, 4H), 2.86 (s, 6H), 3.85 (d, 2H, J~2 Hz), 3.86 (s, 6H), 5.1 (s, 2H), 7.14 (s, 2H), 7.60 (s, 4H), 8.44 (m, 1H), 11.18 (s, 1H). LCMS m/z 481.2 (MH+; 99%).

EXAMPLE 15

3,5-Dimethoxy-4-(2-methylpropoxy)-N-[(1-dimethylaminocyclopentyl)methyl]benzamide Synthesised from (1-dimethylaminocyclopentyl)methylamine and 3,5-dimethoxy-4-(2-methylpropoxy) benzoyl chloride following the procedure as described in Example 1 (d). The crude product was purified by LCMS and isolated as the trifluoroacetate salt. $^1$H NMR (CDCl$_3$) δ: 1.01 (d, 6H, J~2 Hz), 1.85 (m, 4H), 2.04 (m, 4H), 2.79 (s, 6H), 3.76 (d, 2H, J~3 Hz), 3.85 (m, 3H), 3.95 (s, 6H), 7.50 (s, 2H), 8.74 (m, 1H), 12.34 (s, 1H). LCMS m/z 379.4 (MH+; 100%).

EXAMPLE 16

4-Benzyloxy-3,5-dimethyl-N-[(1-dimethylaminocycloheptyl)methyl]benzamide

1-Dimethylamino-1-cycloheptylcarbonitrile was prepared from cycloheptanone (2.0 mL, 0.017 mol) by the method used in Example 1 (a) as a clear oil in 70% yield. $^1$H NMR (CDCl$_3$) δ 1.71 (m, 3H), 1.98 (m, 5H), 2.33 (s, 6H), 2.51 (m, 4H). MS m/z 140.2 (M-26(CN)), and reduced by the method used in example 1 (b) to give to (1-dimethylaminocycloheptyl)methylamine as a clear oil in 48% yield. MS 171.4 (MH$^+$). Subsequent coupling of this amine (0.05 g, 0.29 mmol) and 4-butyloxy-3,5-dimethylbenzoyl chloride (0.081 g, 0.29 mmol) by the method used in Example 1 (d) gave the title compound, which was purified by HPLC and isolated as the trifluoroacetate salt, in 0.026 g yield (17%). $^1$H NMR (CDCl$_3$) δ: 1.62 (m, 4H), 1.70 (m, 4H), 1.93 (d, 4H, J~3 Hz), 2.30 (s, 6H), 2.84 (d, 6H, J~3 Hz), 3.89 (d, 2H, J~3 Hz), 4.82 (s, 2H): 7.38 (m, 3H), 7.48 (m, 2H), 7.59 (s, 2H), 8.15 (m, 1H), 11.05 (s, 1H). LCMS m/z 409.2 (MH+; 100%).

EXAMPLE 17

4-n-Propyloxy-3,5-dimethoxy-N-[(1-dimethylaminocyclohexyl)methyl]benzamide

Synthesised from 1-(dimethylaminocyclohexyl)methylamine and 4-n-propyloxy-3,5-dimethoxy benzoyl chloride[5] following the procedure described in Example 1 (d) and purified by LCMS to obtain the product as a trifluoroacetate salt. $^1$H NMR (CDCl$_3$) δ: 0.99 (t, 3H, J=4 Hz), 1.16 (m, 1H), 1.60 (m, 2H), 1.71 (m, 2H), 1.76 (m, 3H), 1.82 (m, 2H), 2.09 (d, 2H, J=4 Hz), 2.79 (m, 6H), 3.96 (s, 6H), 3.98 (m, 2H), 4.06 (d, 2H, J=3 Hz), 7.53 (s, 2H), 8.78 (m, 1H), 11.95 (s, 1H). LCMS m/z 379.4 (MH$^+$; 99.9%). HRMS (FAB) calc. 379.2569, found 379.2594.

EXAMPLE 18

3,5-Dimethoxy-4-(2-phenylethoxy)-N-[(1-dimethylaminocyclopentyl)methyl]benzamide Synthesised from 2-phenylethyl bromide and 3,5-dimethoxy-4-hydroxy-N-[(1-dimethylaminocyclopentyl)methyl]benzamide following the procedure as described in Example 10 (b). The crude product was purified by HPLC and isolated as the trifluoroacetate salt. $^1$H NMR (CDCl$_3$) δ: 1.85 (m, 4H), 1.98 (m, 4H), 2.87 (d, 6H, J~2 Hz), 3.08 (t, 2H, J~3 Hz), 3.85 (s, 6H), 3.86 (m, 2H), 4.25 (t, 2H, J~3 Hz), 7.11 (s, 2H), 7.21 (m, 1H), 7.26 (m, 4H), 8.34 (m, 1H), 10.95 (s, 1H). LCMS m/z 427.2 (MH+; 86%).

EXAMPLE 19

3,5-Dimethoxy-4-(1-naphthyl)methoxy-N-[(1-dimethylaminocyclopentyl)methyl]benzamide Synthesised from 1-naphthylmethyl bromide and 3,5-dimethoxy-4-hydroxy-N-[(1-dimethylaminocyclopentyl)methyl]benzamide following the procedure as described in Example 10 (b). The crude product was purified by HPLC and isolated as the trifluoroacetate salt. $^1$H NMR (CDCl$_3$) δ: 1.83 (m, 4H), 1.94 (m, 4H), 2.80 (d, 6H, J~2 Hz), 3.83 (s, 6H), 3.84 (m, 2H), 5.47 (s, 2H), 7.17 (s, 2H), 7.42 (t, 1H, J~3 Hz), 7.49 (t, 1H, J~3 Hz), 7.55 (m, 2H), 7.83 (m, 2H), 8.45 (d, 1H, J~3 Hz), 8.55 (m, 1H), 11.75 (s, 1H). LCMS m/z 463.2 (MH+; 100%).

EXAMPLE 20

3,5-Dimethyl-4-(3-thienyl)methoxy-N-[(1-dimethylaminocyclopentyl)methyl]benzamide Synthesised from 3-thienylmethyl bromide and 3,5-dimethyl-4-hydroxy-N-[(1-dimethylaminocyclopentyl)methyl]benzamide following the procedure as described in Example 10 (b). The crude product was purified by SPE chromatography. $^1$H NMR (CDCl$_3$) δ: 1.41 (m, 2H), 1.65 (m, 4H), 1.83 (m, 2H), 2.27 (s, 6H), 2.31 (s, 6H), 3.44 (d, 2H, J~2 Hz), 4.85 (s, 2H), 6.88 (s, 1H), 7.16 (m, 1H), 7.26 (m, 1H), 7.34 (m, 2H), 7.45 (s, 2H). LCMS m/z 387.0 (MH+; 98%).

EXAMPLE 21

4-Cyclopentyloxy-3,5-dimethoxy-N-[(1-dimethylaminocyclopentyl)methyl]benzamide

Synthesised from 1-(dimethylaminocyclopentyl)methylamine and 4-cyclopentyloxy-3,5-dimethoxybenzoyl chloride following the procedure as described in Example 10 (b). The crude product was purified by LCMS and isolated as the trifluoroacetate salt. $^1$H NMR (CDCl$_3$) δ 1.56 (m, 3H), 1.66 (m, 3H), 1.88 (m, 8H), 2.02 (m, 2H), 2.79 (s, 6H), 3.85 (d, 2H, J~2 Hz), 3.94 (s, 6H), 4.89 (m, 1H), 7.50 (s, 2H), 8.74 (m, 1H), 12.36 (s, 1H). LCMS m/z 391.2 (MH+; 98.7%).

EXAMPLE 22

3,4,5-Trimethoxy-N-[(1-dimethylaminocyclohexyl)methyl]benzamide

Prepared from (1-dimethylaminocyclohexyl)methylamine (0.103 g, 6.59 mmol) and trimethoxybenzoyl chloride (0.152 g, 6.59 mmol) by the method used in Example 1(d). The crude product (0.18 g) was chromatographed over silica gel (1.8 g) eluting with dichloromethane/ether (gradient; 100% DCM to 100% ether) before being converted to the hydrochloride salt using methanolic hydrogen chloride. The hydrochloride salt was crystallised from methanol/ether mixture (4/1, v/v) to obtain 0.11 g (43%) of the title compound as a colourless solid. $^1$H NMR (MeOD) δ: 1.37 (m, 1H), 1.77 (m, 7H), 1.99 (m, 2H), 2.96 (s, 6H), 3.88 (s, 3H), 3.90 (s, 2H), 3.93 (s, 6H), 7.30 (s, 2H). LCMS m/z 351.4 (MH$^+$; 96.99%). HRMS (FAB) calc. 351.22783, found 351.2280. ($C_{19}H_{30}N_2O_4 \cdot 0.95HCl \cdot 0.85H_2O$) C, H, N, Cl.

EXAMPLE 23

Glycine Uptake Assays

Glycine uptake assays were performed as described by Morrow et al. (*FEBS Lett*. 1998, 439, 334–340) using CHO cells stably transfected with either hGlyT-1b or hGlyT-2. Cells were grown in 96 well microtitre plates (30,000 cells/well) for 24–48 hours before removal of culture medium and addition of Hanks Balanced Salt Solution (HBSS) containing [$^3$H]-glycine (30 μM) and varying concentrations of test compounds. Plates were incubated at 37° C. for 10 minutes and uptake terminated by washing three times with ice-cold HBSS. After removal of excess liquid, scintillation cocktail was added to each well, prior to counting in a plate counter. Data were analysed using the GraphPad Prism™ analysis package and the sigmoid dose-response curve fitting option to produce $IC_{50}$ (the concentration of test compound producing 50% inhibition of uptake) values.

TABLE I

Inhibition of glycine transport by hGlyT-2

| Ex. | COMPOUND | $IC_{50}$ (nM) |
|---|---|---|
| 1 | 4-Butyloxy-3,5-dimethoxy-N-[(1-dimethylaminocyclohexyl)methyl] benzamide | 214 |
| 2 | 4-Benzyloxy-3,5-dimethoxy-N-[(1-dimethylaminocyclopentyl)-methyl] benzamide | 16 |
| 4 | 4-n-Butyloxy-3,5-dimethoxy-N-[(1-ethylmethylamino)cyclohexyl]-methyl] benzamide (reference compound) | 1321 |
| 5 | 4-Benzyloxy-3,5-dimethoxy-N-[(1-dimethylaminocyclohexyl)methyl] benzamide | 84 |
| 7 | 4-n-Butyloxy-3,5-dimethoxy-N-[(1-dimethylaminocyclopentyl)-methyl] benzamide | 77 |
| 8 | 4-Benzyloxy-3,5-dimethyl-N-[(1-dimethylaminocyclobutyl)-methyl]benzamide | 16 |
| 9 | 4-Benzyloxy-3,5-dimethyl-N-[(1-dimethylaminocyclopentyl)-methyl]benzamide | 27 |
| 10 | 3,5-Dimethoxy-4-(4-methylbenzyloxy)-N-[(1-dimethylaminocyclopentyl)methyl] benzamide | 30 |
| 11 | 3,5-Dimethoxy-4-(1-phenylethoxy)-N-[(1-dimethylaminocyclopentyl)methyl] benzamide | 35 |
| 12 | 4-(4-Chlorobenzyloxy)-3,5-dimethoxy-N-[(1-dimethylaminocyclopentyl) methyl]benzamide | 44 |
| 13 | 4-(Cyclohexylmethoxy)-3,5-dimethoxy-N-[(1-dimethylaminocyclohexyl)methyl]benzamide | 71 |
| 14 | 3,5-Dimethoxy-4-(4-trifluoromethyl)benzyloxy-N-[(1-dimethylaminocyclopentyl)methyl]benzamide | 76 |
| 15 | 3,5-Dimethoxy-4-(2-methylpropoxy)-N-[(1-dimethylaminocyclopentyl)methyl]benzamide | 79 |
| 16 | 4-Benzyloxy-3,5-dimethyl-N-[(1-dimethylaminocycloheptyl)-methyl]benzamide | 92 |
| 18 | 3,5-Dimethoxy-4-(2-phenylethoxy)-N-[(1-dimethylaminocyclopentyl)methyl]benzamide | 156 |
| 19 | 3,5-Dimethoxy-4-(1-naphthyl)methoxy-N-[(1-dimethylaminocyclopentyl)methyl]benzamide | 215 |
| 20 | 3,5-Dimethyl-4-(3-thienylmethoxy)-N-[(1-dimethylaminocyclopentyl)methyl]benzamide | 32 |
| 21 | 4-Cyclopentyloxy-3,5-dimethoxy-N-[(1-dimethylaminocyclopentyl)methyl] benzamide | 329 |
| 22 | 3,4,5-Trimethoxy-N-[(1-dimethylaminocyclohexyl)methyl] benzamide [U.S. Pat. No. 3,975,443] | >10000 |

All compounds were also tested for their selectivity in the GlyT-1 assay and found to be inactive at 10 μM concentration.

EXAMPLE 24

Chung Model of Neuropathy

The withdrawal threshold of naive rats was determined on day 0, using calibrated von Frey filaments (2.6–167 mN) applied to the plantar surface of the paw using an up and down method. The interval between each application was 3–4s. The rats were then anaesthetised under gaseous anaesthesia and the L5 spinal nerve tightly ligated. After a period of 3–5 days the withdrawal thresholds were measured. The test compound or vehicle was then administered and the animals' withdrawal thresholds measured at 20, 40, 60, 90, 120 and 180 min after drug administration. In an initial study, four groups of animals (n≧9/group) were used. All drugs were given subcutaneously in a volume of 2 ml/kg. Single doses of drug were used based on published data. The four groups were vehicle (saline), 4-Benzyloxy-3,5-dimethoxy-N-[(1-dimethylaminocyclopentyl)methyl]benzamide (Example 2) (20 mg/kg) and two positive controls: morphine sulphate (2 mg/kg) and gabapentin (50 mg/kg). Data were compared among groups using the Kruskal-Wallis one-way analysis of variance, a non-parametric statistical test, followed by the Dunn's test for multiple comparisons. Statistical significance was accepted if $P<0.05$.

In vivo Results (Chung Model of Neuropathy)

Tight ligation of the L5 spinal nerve resulted in a decrease in withdrawal threshold from 11.9±0.6 g before surgery to 0.8±0.1 g (n=37) after surgery. All of the drugs tested resulted in a significant increase in withdrawal threshold when compared to the pre-drug value. Withdrawal thresholds increased to 4.2±1.5 g (n=10), 3.2±1.5 g (n=9) and 4.7±1.15 g (n=9) twenty minutes after injection of morphine, gabapentin or 4-benzyloxy-3,5-dimethoxy-N-[(1-dimethylaminocyclopentyl)methyl]benzamide (Example 2). In contrast, twenty min after vehicle injection no change in withdrawal threshold was observed (0.6±0.2; n=10). This increase in withdrawal threshold was significant for up to 90 min after drug injection.

LITERATURE REFERENCES (1) Yang, D.; Bremont, B.; Shen, S.; Kefi, S. and Langlois, M. Serotoninergic properties of new conformationally restricted benzamides. *Eur. J. Med. Chem.* 1996, 31, 231–239.

(2) Moehrle, H. and Feil, R. Aminolysis of 2-phenylaziridine. *Tetrahedron*, 1971, 27, 1033–1041.

(3) Tilford, C. H; MacKenzie, R. D; Blohm, T. R. and Grisar, J. M. Substituted 3,4-pentadienyldiamines as inhibitors of platelet aggregation. *J. Med. Chem.* 1973, 16, 688–693.

(4) Hatakeyama, H. and Kasuga, K. Synthesis and liquid crystalline properties of homologous series having guaiacyl structure as central linkage: 4-(4'-n-alkoxy-3'-methoxybenzoyl)oxybenzoic acids. *Cellul. Chem. Technol.* 1985, 19, 37–45.

(5) Kasztreiner, E.; Vargha, L and Borsy, J. Derivatives of alkoxybenzoic acids. III. Basic esters of 4-alkoxy-3,5-dimethoxy- and 2-alkoxy-3,4-dimethoxy-benzoic acids with papaverine-like spasmolytic action. *Acta Chim. Acad. Sci. Hung.* 1967, 51, 327–337.

(6) Klick, S. and Herrmann, K. Glucosides and glucose esters of hydroxybenzoic acids in plants. *Phytochemistry*, 1988, 27, 2177–2180.

The invention claimed is:

1. A N-[(1-dimethylaminocycloalkyl)methyl]benzamide derivative having the general formula I

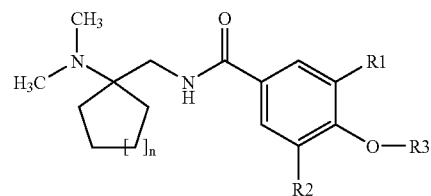

Formula I wherein
n is 0, 1, 2 or 3;
$R_1$ and $R_2$ are independently H, $(C_{1-4})$alkyl or $C_{(1-4)}$ alkoxy;
$R_3$ is $(C_{3-8})$alkyl, $(C_{4-7})$ cycloalkyl, $(C_{4-7})$ cycloalkyl $(C_{1-3})$alkyl, $(C_{6-12})$aryl$(C_{1-3})$alkyl (wherein the aryl moiety is optionally substituted with 1–3 substituents selected from $(C_{1-4})$alkyl, $(C_{1-4})$alkyloxy, halogen, trifluoromethyl and methoxycarbonyl), or
$(C_{4-9})$heteroaryl$(C_{1-3})$alkyl; or a pharmaceutically acceptable salt thereof.

2. The N-[(1-dimethylaminocycloalkyl)methyl]benzamide derivative according to claim 1, wherein n is 0 or 1.

3. The N-[(1-dimethylaminocycloalkyl)methyl]benzamide derivative according to claim 1, wherein $R_1$ and $R_2$ are independently methyl or methyloxy.

4. The N-[(1-dimethylaminocycloalkyl)methyl]benzamide derivative according to claim 1, which is selected from the group consisting of:
-4-benzyloxy-3,5-dimethoxy-N-[(1-dimethylaminocyclopentyl)methyl]benzamide;
-4-benzyloxy-3,5-dimethyl-N-[(1-dimethylaminocyclobutyl)methyl]benzamide;
-4-benzyloxy-3,5-dimethyl-N-[(1-dimethylaminocyclopentyl)methyl]benzamide;
-3,5-dimethoxy-4-(4-methylbenzyloxy)-N-[(1-dimethylaminocyclopentyl)methyl]benzamide;
-3,5-dimethoxy-4-(1-phenylethoxy)-N-[(1-dimethylaminocyclopentyl)methyl]benzamide; and
-4-(4-chlorobenzyloxy)-3,5-dimethoxy-N-[(1-dimethylaminocyclopentyl)methyl]benzamide.

5. A pharmaceutical composition, comprising:
the N-[(1-dimethylaminocycloalkyl)methyl]benzamide derivative according to claim 1, or a pharmaceutically acceptable salt thereof, and
pharmaceutically acceptable auxiliaries.

6. A method of treating a neurological disorder which is responsive to inhibition of the GlyT-2 transporter, comprising:
administering to a mammal an effective amount of a N-[(1-dimethylaminocycloalkyl)methyl]benzamide derivative according to formula I of claim 1.

7. The method according to claim 6, wherein the mammal is a human.

8. A method of selectively inhibiting a GlyT-2 transporter in a mammal, comprising:
administering an amount of the N-[(1-dimethylaminocycloalkyl)methyl]benzamide derivative according to claim 1, to effect the inhibition of a GlyT-2 transporter in a mammal.

9. The method according to claim 8, wherein the mammal is a human.

* * * * *